United States Patent [19]

Malamas

[11] Patent Number: 4,983,613

[45] Date of Patent: Jan. 8, 1991

[54] ISOQUINOLINE ACETIC ACIDS AND ACETYL CARBAMATES USEFUL AS ALDOSE REDUCTASE INHIBITORS

[75] Inventor: Michael S. Malamas, Jamison, Pa.

[73] Assignee: American Home Products Corporation, New York, N.Y.

[21] Appl. No.: 341,608

[22] Filed: Apr. 21, 1989

[51] Int. Cl.$^5$ .................. A61K 31/47; C07D 401/06
[52] U.S. Cl. ................................. 514/309; 546/142
[58] Field of Search .................. 546/142; 514/309

[56] References Cited

PUBLICATIONS

Fournier, "Chemical Abstracts", vol. 71, 1969, col. 12989h.
Iida et al., "Chemical Abstracts", vol. 106, 1987, col. 106:5298v.

Primary Examiner—Glennon H. Hollrah
Assistant Examiner—James H. Turnipseed
Attorney, Agent, or Firm—Walter Patton

[57] ABSTRACT

This invention relates to isoquinoline acetic acids and acetyl carbamates and their pharmaceutically acceptable salts thereof, to processes for their preparation, to methods for using the compounds, and to pharmaceutical preparations thereof. The compounds have pharmaceutical properties which render them beneficial for the treatment of diabetes mellitus and associated conditions.

11 Claims, No Drawings

ISOQUINOLINE ACETIC ACIDS AND ACETYL CARBAMATES USEFUL AS ALDOSE REDUCTASE INHIBITORS

BACKGROUND OF THE INVENTION

This invention relates to isoquinoline acetic acid and acetyl carbamates and their pharmaceutically acceptable salts thereof, to processes for their preparation, to methods for using the compounds, and to pharmaceutical preparations thereof. The compounds have pharmaceutical properties which render them beneficial for the treatment of diabetes mellitus and associated conditions.

The use of insulin and/or oral hypoglycemic agents in the treatment of diabetes mellitus has prolonged the life of many of these patients. However, their use has not had a demonstrable impact on the development of diabetic complications such as neuropathy, nephropathy, retinopathy, cataracts and vascular disease which accompany the underlying metabolic disorder. There is little question that chronic hyperglycemia plays a major role in the genesis of these complications, and that complete normalization of blood glucose would likely prevent most if not all complications. For a number of reasons, though, chronic normalization of blood glucose has not been achieved with the currently available therapies. The development of diabetic complications has recently been linked to the increased accumulation of tissue sorbitol resulting from chronic hyperglycemia. Therapeutic reduction of sorbitol accumulation could potentially prevent the development of diabetic complications.

In mammals, including humans, the key enzyme involved in the conversion of hexoses to polyols (e.g. the sorbitol pathway) is aldose reductase. J. H. Kinoshita and collaborators [see J. H. Kinoshita et al., Biochem. Biophys. Acta, 158,472(1968) and references cited therein] have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nerves and kidney of diabetic animals, [see A. Pirie and R. van Heyningen, Exp. Eye Res., 3,124 (1964); L. T. Chylack and J. H. Kinoshita, Invest. Ophthal., 8, 401 (1969) and J. D. Ward and R. W. D. Baker, Diabetol., 6 531 (1970)].

SUMMARY OF THE INVENTION

The isoquinoline acetic acids and acetyl carbamates of the present invention are represented by formula (I)

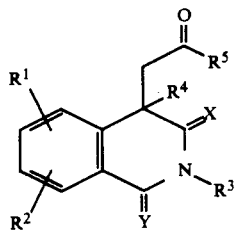

(I)

wherein $R^1$ and $R^2$ are independently hydrogen, alkyl containing 1 to 6 carbon atoms, halogen, lower alkoxy containing 1 to 6 carbon atoms, trifluoromethyl, lower alkylthio wherein lower alkyl contains 1 to 6 carbon atoms, dialkylamino wherein alkyl contains 1 to 6 carbon atoms, nitro, aryl or aryl (lower alkyl) oxy wherein aryl contains 6 to 10 carbon atoms and lower alkyl contains 1 to 6 carbon atoms; $R^3$ is lower alkyl containing 1 to 6 carbon atoms, aryl, aryl (lower alkyl) or halogen substituted aryl (lower alkyl) wherein aryl contains 6 to 10 carbon atoms and lower alkyl contains 1 to 6 carbon atoms, acyl or heterocyclic (lower alkyl) of structural formula

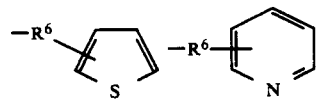

wherein $R^6$ is lower alkylene containing 1 t 3 carbon atoms; $R^4$ is hydrogen, lower alkyl containing 1 to 6 carbon atoms, carboalkoxy wherein alkoxy contains 1 to 3 carbon atoms; $R^5$ is amino, hydroxy, alkoxy containing 1 to 6 carbon atoms, lower alkyl carbamates wherein lower alkyl contains 1 to 6 carbon atoms, aryl carbamates wherein aryl contains 6 to 10 carbon atoms, and aryl(lower alkyl) carbamates wherein lower alkyl contains 1 to 6 carbon atoms; X and Y are oxygen or sulfur, and the pharmaceutically acceptable salts thereof. The fused benzene ring can be replaced by thiophene, pyridine or furan.

Suitable salts of the object compounds (I) are conventional pharmaceutically acceptable salts and may include, but are not limited to, alkali earth metal cations, such as potassium and sodium; ammonium or water-soluble amine addition salts, such as the lower alkylammonium and other base salts with organic amines which are pharmaceutically acceptable; and alkaline earth metal cations such as calcium and magnesium.

A preferred group of compounds of the present invention is represented by formula (II)

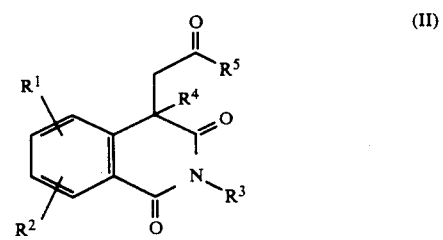

(II)

wherein $R^1$ and $R^2$ are independently hydrogen, alkyl containing 1 to 6 carbon atoms, halogen or trifluoromethyl; $R^3$ is lower alkyl containing 1 to 6 carbon atoms or aryl(lower alkyl) wherein aryl contains 6 to 10 carbon atoms and lower alkyl contains 1 to 6 carbon atoms; $R^4$ is hydrogen; $R^5$ is amino, hydroxy, lower alkyl carbamates wherein lower alkyl contains 1 to 6 carbon atoms, aryl carbamates wherein aryl contains 6 to 10 carbon atoms, and the pharmaceutically acceptable salts thereof.

A more preferred group of compounds of the present invention is represented by formula (III)

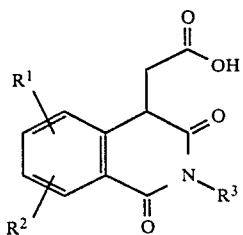

(IV)

wherein R¹ and R² are hydrogen or halogen; R³ is lower alkyl containing 1 to 6 carbon atoms or halogen substituted aryl (lower alkyl) wherein aryl contains 6 to 10 carbon atoms and lower alkyl contains 1 to 6 carbon atoms, and the pharmaceutically acceptable salts thereof.

A second preferred group of compounds of the present invention is represented by formula (IV)

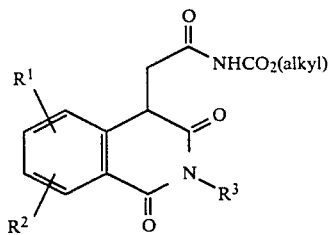

(III)

wherein R¹ and R² are hydrogen or halogen; R³ is halogen substituted aryl (lower alkyl) wherein aryl contains 6 to 10 carbon atoms lower alkyl contains 1 to 6 carbon atoms, and the pharmaceutically acceptable salts thereof.

The most preferred compounds of the present invention are set forth below:

[[2-[(4-bromo-2-fluorophenyl)methyl]-6-fluoro-1,2,3,4-tetrahydro-1,3-dioxo-4-isoquinolinyl]acetyl]carbamic acid methyl ester;

[(1,2,3,4-tetrahydro-2-methyl-1,3-dioxo-4-isoquinolinyl)acetyl]carbamic acid methyl ester;

[(6-chloro-1,2,3,4-tetrahydro-2-methyl-1,3-dioxo-4-isoquinolinyl)acetyl]carbamic acid methyl ester;

[(6-chloro-1,2,3,4-tetrahydro-2-methyl-1,3-dioxo-4-isoquinolinyl)acetyl]carbamic acid ethyl ester;

[(7-chloro-1,2,3,4-tetrahydro-2-methyl-1,3-dioxo-4-isoquinolinyl)acetyl]carbamic acid methyl ester;

2-[(4-bromo-2-fluorophenyl)methyl]-6-fluoro-1,2,3,4-tetrahydro-1,3-dioxo-4-isoquinolineacetic acid;

2-[(4-bromo-2-fluorophenyl)methyl]-1,2,3,4-tetrahydro-1,3-dioxo-4-isoquinolineacetic acid; and the pharmaceutically acceptable salts thereof.

A method is provided for preventing or relieving diabetes mellitus associated complications in a diabetic mammal by administering to said mammal a prophylactic or alleviating amount of the compound of formula (I). Such complications include neuropathy, nephropathy, retinopathy, keratopathy, diabetic uveitis and cataracts.

The compounds of formula (I), when admixed with a pharmaceutically acceptable carrier, form a pharmaceutical composition which can be used according to the preceding method.

DETAILED DESCRIPTION OF THE INVENTION

The isoquinoline acetic acids and acetyl carbamates of this invention may be administered to mammals, for example, man, cattle or rabbits, either alone or in dosage forms, i.e., capsules or tablets, combined with pharmacologically acceptable excipients.

The compounds of this invention may be orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the isoquinoline acetic acids and acetyl carbamates will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05–1.0% solution may be administered dropwise in the eye. The frequency of instillation varies with the subject under treatment from a drop every two or three days to once daily. For oral or parenteral administration a preferred level of dosage ranges from about 1.0 mg to about 100 mg per kilo of body weight per day, although aforementioned variations will occur. However, a dosage level that is in the range of from about 5 mg to 50 mg per kilo of body weight per day is most satisfactory.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The isoquinoline acetic acids and acetyl carbamates also can be used in combination with insulin or oral hypoglycemic agents to produce a beneficial effect in the treatment of diabetes mellitus. In this instance, commercially available insulin preparations or oral hypoglycemic agents, exemplified by acetohexamide, chloropropamide, tolazamide, tolbutamide and phenformin, are suitable. The compounds herein can be administered sequentially or simultaneously with insulin or the oral hypoglycemic agent. Suitable methods of administration, compositions and doses of the insulin preparation or oral hypoglycemic agent are described in medical textbooks; for instance, *Physicians' Desk Reference*, 42 ed., Medical Economics Co., Oradell, N.J., U.S.A., 1988.

The aldose reductase inhibiting property of the compounds of this invention and the utilization of the compounds in preventing, diminishing and alleviating diabetic complications are demonstrable in experiments using galactosemic rats, see Dvornik et al., Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (Rodent Laboratory Chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of the galactose in the diet of the treated groups was the same as that for the untreated galactosemic group.

(b) After four days, the animals were killed by euthanization. The lenses were removed from the eyes and weighed. The sciatic nerves were dissected as completely as possible and weighed. Both tissues when frozen can be kept up to two weeks before being analyzed for dulcitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240,877 (1965). In the present case the procedure of Hayman and Kinoshita was modified in that the final chromatography step was omitted in the preparation of the enzyme from bovine lens.

The following tabulated results show that the isoquinoline acetic acids and acetyl carbamates of this invention show the property that they are active both in vitro and in vivo and diminish the accumulation of dulcitol in the lenses and sciatic nerves of rats fed galactose. The figures under L and N represent the percentage decrease of dulcitol accumulation in the tissues of the lens and sciatic nerve, respectively, for treated rats as compared to untreated rats.

TABLE 1

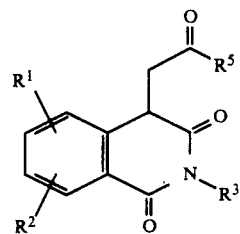

| | | | | | | % Lowering Ducitol Accumulation In vivo | |
|---|---|---|---|---|---|---|---|
| $R^1$ | $R^2$ | $R^3$ | $R^5$ | % Inhibition In vitro | Dose mg/kg | Lens | Nerve |
| -6F | —H | benzyl-2F-4Br | —OH | 96 ($10^{-5}$M) 91 ($10^{-6}$M) 86 ($10^{-7}$M) 80 (4 × $10^{-8}$M) | 25 | NS | 47 |
| —H | —H | benzyl-2F-4Br | —OH | 94 ($10^{-5}$M) 91 ($10^{-6}$M) 88 ($10^{-7}$M) 50 (4 × $10^{-8}$M) | 103 | NS | NS |

TABLE 1-continued

[Structure with R¹, R² on benzene ring, CH group connecting to CH₂-C(=O)-R⁵ and C(=O)-N(R³)-C(=O)]

| R¹ | R² | R³ | R⁵ | % Inhibition In vitro | Dose mg/kg | % Lowering Ducitol Accumulation In vivo Lens | Nerve |
|---|---|---|---|---|---|---|---|
| -6F | —H | [2-F, 4-Br benzyl] | —NHCO$_2$CH$_3$ | 55 ($10^{-5}$M) 18 ($10^{-6}$M) | 26 | NS | 78 |
| -6Cl | —H | —CH$_3$ | —NHCO$_2$C$_2$H$_5$ | 14.5 ($10^{-5}$M) | 24.5 | NS | 34 |
| -6Cl | —H | —CH$_3$ | —NHCO$_2$CH$_3$ | 64.5 ($10^{-5}$M) 26.6 ($10^{-6}$M) | 25 86.1 | 24 55 | 53 81 |
| —H | -7Cl | —CH$_3$ | —NHCO$_2$CH$_3$ | 50($10^{-5}$M) 17 ($10^{-6}$M) | 24.3 | NS | 28 |
| —H | —H | —CH$_3$ | —NHCO$_2$CH$_3$ | 61 ($10^{-5}$M) 11 ($10^-$M) | 26.8 85.0 | NS 37.2 | 21.2 58.6 |

NS = not significant.

THE PROCESS

The isoquinoline acetic acids and acetyl carbamates were prepared by the following reaction scheme.

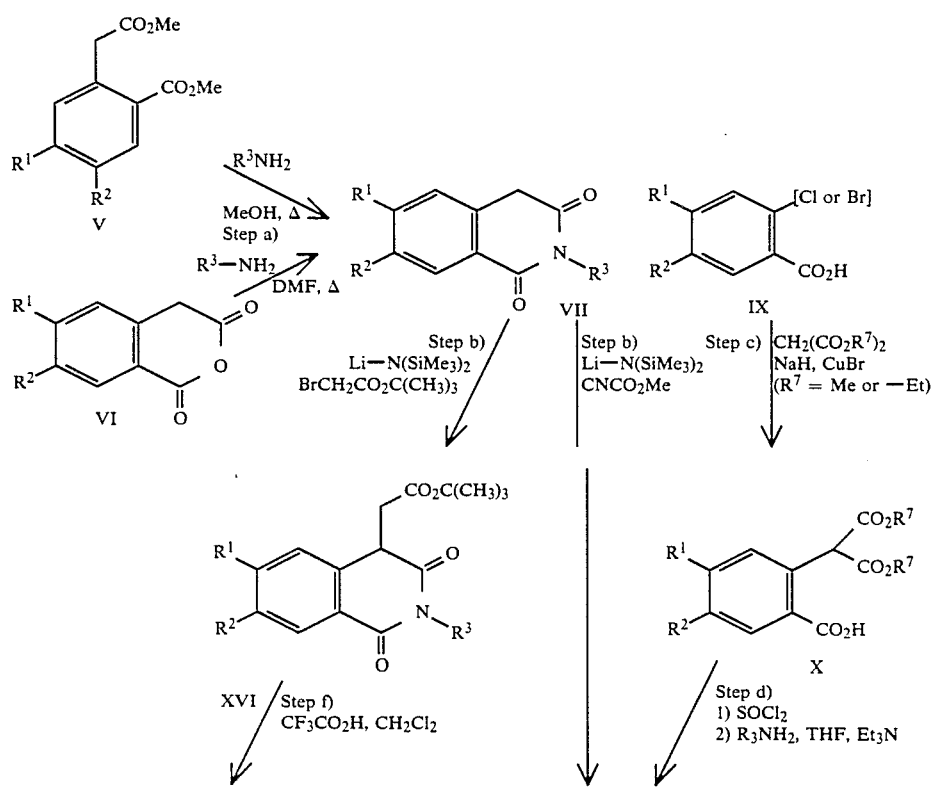

-continued

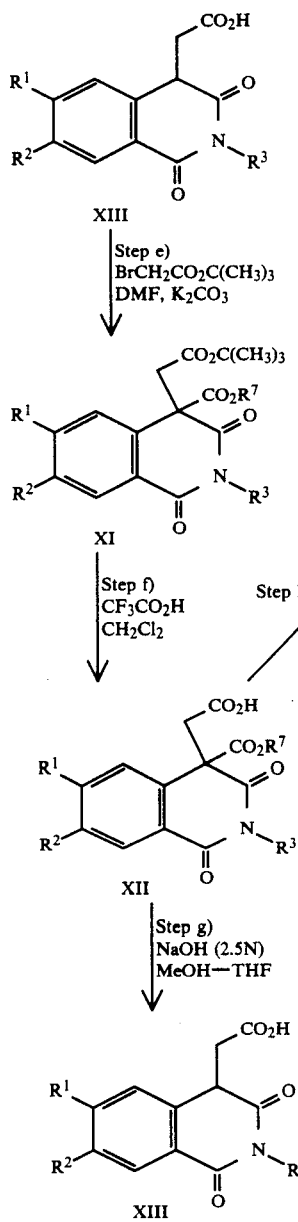

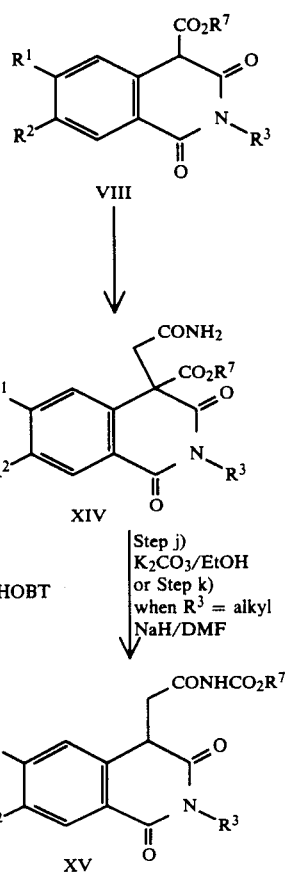

wherein $R_1$ and $R_2$ are hydrogen, halogen; $R_3$ is alkyl or aralkyl; $R_5$ is hydroxy or alkyl carbamate; $R_7$ is methyl or ethyl and X, Y are oxygen.

The process for the production of the compounds of formula (I), wherein $R^1$ and $R^2$ are halogen (fluorine, chlorine) or hydrogen; $R^3$ is alkyl (methyl) or aralkyl (4-bromo-2-fluorobenzyl); $R_4$ is hydrogen; $R_5$ is hydroxy or alkyl (methyl, ethyl) carbamate; X, Y are oxygen, comprises:

Step (a)

Reacting either homophthalic acid dimethyl ester of formula (V) or homophthalic anhydride of formula (VI), wherein $R^1$ and $R^2$ are as defined above, with an amine $R^3$—$NH_2$, wherein $R^3$ is as defined above, to produce the homophthalimide of formula (VII), wherein $R^1$, $R^2$, and $R^3$ are as defined above.

The homophtalic acid dimethyl esters of formula (V) and the homophthalic anhydrides of formula (VI) required for the present invention are commercially available compounds or can be prepared by known methods.

The homophthalic acid dimethyl ester compound (V) can be reacted with a saturated methanolic ammonium solution in a pressure vessel and temperature in the range of 60°-80° C.

The homophthalic anhydride compound (VI) can be reacted with an amine at high temperature 160°-180° C. in a conventional solvent which does not adversely influence the reaction, such as N,N-dimethylformadide. However, reaction of a volatile amine with the homophthalic anhydride compound (VI) can proceed by reaction of a saturated tetrahydrofuran solution of the appropriate amine with homophthalic anhydride at room temperature and subsequent removal of the volatiles and introduction of N,N-dimethylformamide as the solvent. Further reaction at high temperature (160°-180° C.) is required to produce the compound of formula (VII).

Step (b)

The compound of formula (VII) wherein $R^1$, $R^2$, and $R^3$ are as defined above is reactied with a base, for example lithium bis(trimethylsilyl)amide in a conventional solvent which does not adversely influence the reaction, for example tetrahydrofuran, and subsequent addition of a reactive carbomethoxylating agent, such as methyl cyanoformate or any alkylating agent such as tert-butyl bromoacetate, produces the compounds of formula (VIII) and (XVI) respectively, wherein $R^1$, $R^2$, and $R^3$ are as defined above.

Step (c)

Reacting either 2-bromobenzoic acid or 2-chlorobenzoic acid of formula (IX) wherein $R^1$ and $R^2$ are as defined above with dimethyl or diethyl malonate and NaH in the presence of a catalytic amount of CuBr to produce the propanedioic acid dimethyl or diethyl ester of formula (X) wherein $R^1$, $R^2$, $R^3$ and $R^7$ are as defined above. The 2-bromobenzoic acids or 2-chlorobenzoic acids of formula (IX) required for the present invention are commercially available compounds or can be prepared by known methods.

Step (d)

The propanedioic acid dimethyl or diethyl ester of formula (X) can be reacted with thionyl chloride under refluxing conditions to produce the corresponding acid chloride which upon treatment with an amine $R^3$—$NH_2$ in the presence of triethylamine in a conventional solvent which does not adversely influence the reaction, for example, tetrahydrofuran, can produce the compound of formula (VIII) wherein $R^1$, $R^2$, $R^3$ and $R^7$ are as defined above.

Step (e)

The compound of formula (VIII), wherein $R^1$, $R^2$, $R^3$ and $R^7$ are as defined above is reacted with an inorganic base, such as potassium carbonate, in a conventional solvent which does not adversely influence the reaction, N,N-dimethylformamide, and subsequent addition of tert-butyl bromoacetate produces the compound of formula (XI), wherein $R^1$, $R^2$, $R^3$ and $R^7$ are as defined above.

Step (f)

The compounds of formula (XI) and (XVI), wherein $R^1$, $R^2$, $R^3$ and $R^7$ are as defined above are hydrolyzed with an organic acid, such as trifluoroacetic acid, in a conventional solvent which does not adversely influence the reaction, for example, methylene chloride, to produce the compound of formula (XII) and (XIII), respectively, wherein $R^1$, $R^2$, $R^3$ and $R^7$ are as defined above.

Step (g)

The compound of formula (XII) wherein $R^1$, $R^2$, $R^3$ and $R^6$ are as defined above is reacted with an aqueous inorganic base, such as sodium hydroxide in an alcohol-THF solution, to produce the compound of formula (XIII) wherein $R^1$, $R^2$ and $R^3$ are as defined above.

Step (h)

The compound of formula (XII) wherein $R^1$, $R^2$, $R^3$ and $R^7$ are as defined above, can be reacted with thionyl chloride under refluxing conditions to produce the corresponding acid chloride, which upon treatment with a saturated tetrahydrofuran ammonium solution can produce the compound of formula (XIV), wherein $R^1$, $R^2$, $R^3$ and $R^7$ are as defined above.

Step (i)

The compound of formula (XII) wherein $R^1$, $R^2$, $R^3$ and $R^7$ are as defined above, is reacted with a coupling agent, such as 1-(3-dimethylaminopropyl)-3-ethylcarbodiimide(DCC')/1-hydroxybenzotriazole, in a conventional solvent which does not adversely influence the reaction, for example, N,N-dimethylformamide, and subsequent addition of a tetrahydrofuran ammonium solution produces the compound of formula (XIV), wherein $R^1$, $R^2$, $R^3$ and $R^7$ are as defined above.

Step (j)

The compound of formula (XIV) wherein $R^1$, $R^2$, $R^3$ and $R^7$ are as defined above is reacted with an inorganic base such as potassium carbonate in ethanolic solution to produce the compound of formula (XV) wherein $R^1$, $R^2$, $R^3$ and $R^7$ are as defined above.

Step (k)

The compound of formula (XIV), wherein $R^1$, $R^2$ and $R^7$ are as defined above, and $R^3$ is alkyl is reacted with a base, such as sodium hydride, in a conventional solvent which does not adversely influence the reaction, for example, N,N-dimethylformamide, to produce the compound of formula (XV), wherein $R^1$, $R^2$ and $R^7$ are as defined above and $R^3$ is an alkyl, as defined above.

The chemical bases which are used as reagents in this invention to prepare the aforementioned pharmaceutically acceptable salts are those which form nontoxic salts with the various herein described acidic isoquinoline acetic acids and acetyl carbamates. These particular non-toxic base salts are of such a nature that their cations are said to be essentially nontoxic in character over the wide range of dosage administered. Examples of such cations include those of sodium, potassium, calcium, and magnesium. These salts can easily be prepared by simply treating the aforementioned acidic isoquinoline acetic acids and acetyl carbamates with an aqueous solution of the desired pharmacologically acceptable cation and then isolating by filtration or evaporation the resulting salts.

Alternatively, they may also be prepared by mixing organic solutions of the said acidic compounds and the desired alkali metal hydride together and then isolating the resulting salts by precipitation in non-polar solvent. In either case, stoichiometric quantities of reagents must be employed in order to ensure completeness of reaction and maximum production yields with respect to the desired final product.

The following Examples further illustrate this invention.

EXAMPLE 1

[(1,2,3,4-Tetrahydro-2-methyl-1,3-dioxo-4-isoquinolinyl)acetyl]carbamic Acid Methyl Ester Step (a): Preparation of 2-Methyl-1,3(2H, 4H)-isoquinolinedione Anhydrous monomethylamine was passed through a solution of homophthalic anhydride (10.0 g, 61.73 mmol) in anhydrous THF (200 mL) for 10 minutes. The formed suspension was stirred for 1 hour and the volatiles were removed in vacuo. The residue was taken in DMF (200 mL) and the suspension was stirred at 180° C. for 10 hours. After cooling, the brownish solution was poured into $H_2O$, extracted with EtOAc, and dried over $MgSO_4$. The crude product was recrystallized from acetone/ether/hexane (at 0° C.) to yield a yellow solid m.p. 120°–121° C. (7.9 g, 73.1%).

NMR (DMSO-$d_6$, 400 MHz): δ3.18 (s, 3H, —$NCH_3$), 4.12 (s, 2H, —$CH_2CONCH_3$), 7.36 (d, J=7.67 Hz, 1H, Ar—H̲), 7.47 (t, J=7.37 Hz, 1H, Ar—H̲), 7.64 (t, J=7.45 Hz, 1H, Ar—H̲), 8.02 (d, J=7.87 Hz, 1H, Ar—H̲).

IR (KBr, cm$^{-1}$): 3420 (m), 1720 (s), 1665 (s), 1460 (m), 735 (m).

MS (m/e): 175 (M+), 118 (M+—CONCH$_3$).

Anal. Calcd.: C, 68.56; H, 5.18; N, 8.00. Found: C, 68.57; H, 5.40; N, 8.01.

The following compounds were obtained in substantially the same manner as that of Example 1, Step (a).

2-Propyl-1,3(2H,4H)-isoquinolinedione

NMR (DMSO-d$_6$, 200 MHz): δ0.87 (t, J=7.0 Hz, 3H, —NCH$_2$CH$_2$CH$_3$), 1.56 (m, 2H, —NCH$_2$CH$_2$CH$_3$), 3.81 (t, J=7.0 Hz, 2H, —NCH$_2$CH$_2$CH$_3$), 4.15 (s, 2H, —CH$_2$CON—), 7.4 (t, J=8.2 Hz, 1H, Ar—H, 7.5 (d, J=7.0 Hz, 1H, Ar—H), 7.65 (dt, J=7.0 Hz, 1.0 Hz, 1H, Ar—H), 8.06 (dd, J=7.6 Hz, 0.8 Hz, 1H, Ar—H).

IR (KBr, cm$^{-1}$): 3380 (m), 1720 (s), 1680 (s), 1435 (m), 745 (s).

MS (m/e): 203 (M+), 118 (M+—CONCH$_2$CH$_2$CH$_3$).

Anal. Calcd.: C, 70.92; H, 6.45; N, 6.89. Found: C, 70.68; H, 6.52; N, 6.86.

M.P. 64°-65° C.

2-Butyl-1,3(2H, 4H)-isoquinolinedione

NMR (DMSO-d$_6$, 200 MHz): δ0.89 (t, J=7.2 Hz, 3H, —NCH$_2$CH$_2$CH$_2$CH$_3$), 1.27-1.40(m, 2H, —NCH$_2$CH$_2$CH$_2$CH$_3$), 1.42-1.61 (m, 2H, —NCH$_2$CH$_2$CH$_2$CH$_3$), 3.85 (t, J=7.3 Hz, 2H, —NCH$_2$CH$_2$CH$_2$CH$_3$), 4.14 (s, 2H, —CH$_2$CON—), 7.36 (dt, J=7.6 Hz, 1.2 Hz, 1H, Ar—H), 7.46 (d, J=7.6 Hz, 1H, Ar—H), 7.61, (dt, J=7.6 Hz, 1.6 Hz, 1H, Ar—H), 8.06 (dd, J=7.6 Hz, 2.2 Hz, 1H, Ar—H).

IR (KBr, cm$^{-1}$): 3480 (m), 1720 (s), 1680 (s), 1470 (m), 740 (m).

MS (m/e): 217 (M+), 118 (M+—CONCH$_2$CH$_2$CH$_2$CH$_3$).

Anal. Calcd.: C, 71.87; H, 6.96; N, 6.45. Found: C, 71.81; H, 6.98; N, 6.41.

M.P. 49°-50° C.

Step (a): Preparation of 2-[(3,4-Dichlorophenyl)methyl]-1,3(2H, 4H)-isoquinolinedione To a mixture of homophthalic anhydride (20.0 g, 123.45 mmol) in DMF (300 mL) was added 3,4-dichlorobenzylamine (25.0 g, 142.04 mmol), and the mixture was stirred at 180° C. for 5 hours. After cooling to room temperature, the mixture was poured into H$_2$O, extracted with EtOAc, and dried over MgSO$_4$. The crude product was recrystallized from EtOAc/Et$_2$O/hexane (at 0° C.) to give a brownish solid, m.p. 129°-130° C. (25.21 g, 57.5%).

NMR (DMSO-d$_6$, 400 MHz) δ4.22 (s, 2H, —CH$_2$CO—), 5.0 (s, 2H, —NCH$_2$—), 7.3 (dd, J=8.49 Hz, 1.98 Hz, 1H, Ar—H), 7.4 (d, J=8.54 Hz, 1H, Ar—H), 7.47 (t, J=7.4 Hz, 1H, Ar—H), 7.54 (d, J=8.3 Hz, 1H, Ar—H), 7.57 (d, J=1.7 Hz, 1H, Ar—H), 7.67 (dt, J=8.37 Hz, 0.97 Hz, 1H, Ar—H), 8.03 (d, J=7.83 Hz, 1H, Ar—H).

IR (KBr, cm$^{-1}$): 1650 (s), 1330 (s), 970 (m), 740 (m).

MS (m/e): 319 (M+), 256 (M+—ClCO), 118 (M+—CONH, —CH$_2$C$_6$H$_3$Cl$_2$).

Anal. Calcd.: C, 60.02; H, 3.46; N, 4.37. Found: C, 59.81; H, 3.60; N, 4.36.

The following compounds were obtained in substantially the same manner as that of Example 1, Step (a).

2-[(4-Bromo-2-fluorophenyl)methyl]-1,3(2H, 4H)-isoquinolinedione

NMR (DMSO-d$_6$, 200 MHz): δ4.24 (s, 2H, —CH$_2$CON—), 5.04 (s, 2H, —NCH$_2$—), 7.23 (t, J=7.8 Hz, 1H, Ar—H), 7.3 (d, J=7.65 Hz, 1H, Ar—H), 7.4–7.56 (m, 3H, Ar—H), 7.65 (t, J=7.6 Hz, Ar—H), 8.06 (d, J=7.8 Hz, 1H, Ar—H).

IR (KBr, cm$^{-1}$): 1675(s), 1350(m), 975(m).

MS (m/e): 347 (M+).

Anal. Calcd.: C, 55.19; H, 3.18; N, 4.02. Found: C, 54.83; H, 3.14; N, 4.07.

M.P. 128°-129° C.

Step (b): Preparation of 1,2,3,4-Tetrahydro-2-methyl-1,3-dioxo-4-isoquinolinecarboxylic Acid Methyl Ester To a cold (—78° C.) solution of 2-methyl-1,3(2H, 4H)-isoquinolinedione (5.0 g, 28.57 mmol) in anhydrous THF (100 mL) was added lithium bis(trimethylsily)amide (28.57 mL, 28.57 mmol, 1.0M in THF), over a 10 minute period. After stirring for 3 hours, methyl cyanoformate (2.72 mL, 34.28 mmol) was added and the reaction mixture was allowed to warm up to room temperature. The mixture, during that period, turned dark in color. It was stirred an additional 30 minutes and quenched with H$_2$O. The dark solution was poured into H$_2$O, acidified with HCl (2N), extracted with EtOAc and dried over MgSO$_4$. The crude product was purified by flash chromatography to yield a yellow solid m.p. 130°-131° C. (5.6 g, 84.8%).

NMR (DMSO-d$_6$, 200 MHz) δ [3.24 (s), 3.46 (s), tautomeric 3H, —NCH$_3$], [3.7 (s), 4.03 (s), tautomeric, 3H, —CO$_2$CH$_3$], 7.4–8.45 (tautomeric, 4H, Ar—H).

IR (KBr, cm$^{-1}$): 3400 (brm), 1670 (s), 1600 (s), 1420 (m), 780 (m).

MS (m/e): 233 (M+), 118 (M+—CO$_2$Me, —CONCH$_3$).

Anal. Calcd.: C, 61.80; H, 4.75; N, 6.01. Found: C, 61.62; H, 4.89; N, 5.97.

Step (b): Preparation of 2-[(3,4-Dichlorophenyl)methyl]-1,2,3,4-tetrahydro-1,3-dioxo-4-isoquinolineacetic Acid 1,1-Dimethylethyl Ester To a cold (—78° C.) solution of 2-[(3,4-dichlorophenyl)methyl]-1,3(2H, 4H)-isoquinolinedione (3.0 g, 9.37 mmol) in anhydrous THF (70 mL) was added lithium bis(trimethylsily) amide (9.37 mL, 9.37 mmol, 1.0M in THF), over a 10 minute period. After stirring for 2 hours, tert-butyl bromoacetate (1.82 mL, 11.25 mmol) was added and the reaction mixture was allowed to warm up to room temperature. The mixture, during that period, turned dark in color. It was stirred an additional 2 hours, and was quenched with H$_2$O. The dark solution was poured into H$_2$O, acidified with HCl (2N), extracted with EtOAc, and dried over MgSO$_4$. The crude product was purified by flash chromatography (hexane/EtOAc, 4/1) to yield a yellowish oil (2.1 g, 51.6%).

NMR (DMSO-d$_6$,200 MHz) δ1.08 (s, 9H, —CO$_2$C(CH$_3$)$_3$), 3.34 (m, 2H, —CH$_2$CO$_2$C(CH$_3$)$_3$), 4.42 (t, J=4.2 Hz, 1H CHCH$_2$), 5.08 (s, 9H, —NCH$_2$C$_6$H$_3$Cl$_2$), 7.35-7.8 (m, 6H, Ar—H),8.13 (d, J=8.3 Hz, 1H, Ar—H).

IR (KBr, cm$^{-1}$): 1725 (s), 1675 (s), 1155 (s), 760 (s).

MS (m/e): 433 (M+).

Step (c) Preparation of (2-Carboxyphenyl)propanedioic Acid Dimethyl Ester

To a rapidly stirred, cold suspension (0° C.) of 2-bromobenzoic acid (30.0 g, 149.32 mmol), cuprous bromide (2.14 g, 14.93 mmol) and dimethyl malonate (300 mL) was added NaH (80% in mineral oil, 10.75 g, 358.37 mmol) over a 30 minute period, while a stream of dry N$_2$ was passed over the mixture. After the addition of the NaH had been completed, the mixture was stirred for 10 minutes at room temperature and 30 minutes at 70° C. (external oil bath temperature). At this point, the suspension turned to a solid mass, which was dissolved in H$_2$O (1000 mL). The aqueous layer was extracted with diethyl ether (3×500 mL) and was acidified with HCl (2N). The mixture was extracted with EtOAc and dried over MgSO$_4$. Evaporation gave an off-white solid which was recrystallized from Et$_2$O/hexane (−20° C.) to give a white solid, m.p. 119°-120° C. (34.2 g, 91.0%).

NMR (400 MHz, DMSO-d$_6$): δ 3.67 [s, 6H, —CH(CO$_2$CH$_3$)$_2$], 5.72 [s, 1H, —CH(CO$_2$CH$_3$)$_2$], 7.3 (d, J=7.76 Hz, 1H, Ar—H̲), 7.45 (dt, J=7.66 Hz, 1.12 Hz, 1H, Ar—H̲), 7.6 (dt, J=7.66 Hz, 1.45 Hz, 1H, Ar—H̲), 7.94 (dd, J=7.8 Hz, 1.33 Hz, 1H, Ar—H̲), 13.2 (s, 1H, —CO$_2$H).

IR (KBr, cm$^{-1}$): 3300-2700 (br), 1750 (s), 1730 (s), 1680 (s), 1430 (m), 730 (m).

MS (m/e): 252 (M$^+$), 220 (M$^+$—CH$_3$OH), 188 (M$^+$—2×CH$_3$OH).

Anal. Calcd.: C, 57.14; H, 4.80. Found: C, 57.05; H, 4.78.

The following compound was prepared in substantially the same manner as that of Example 1, Step (c).

(2-Carboxy-6-fluorophenyl)propanedioic Acid Dimethyl Ester

NMR (DMSO-d$_6$, 400 MHz): δ 3.68 [s, 6H, (—CO$_2$Me)$_2$], 5.79 (s, 1H, Ar—CH—), 7.12 (dd, J=10.06 Hz, 2.61 Hz, 1H, Ar—H̲), 7.33 (dt, J=8.48 Hz, 2.64 Hz, 1H, Ar—H̲), 8.03 (dd, 8.77 Hz, 6.17 Hz, 1H, Ar—H̲).

IR (KBr, cm$^{-1}$): 3400-2700 (br), 1730 (s), 1680 (s), 750 (m).

MS (m/e): 270 (M$^+$), 238 (M$^+$—CH$_3$OH), 210 (M$^+$—CH$_3$OH, —CO), 151 (M$^+$—CH$_3$OH—CO—CO$_2$CH$_3$).

M.P. 121.5°-123.0° C.

Step (d): Preparation of 2-[(4-Bromo-2-fluorophenyl)methyl]-1,2,3,4-tetrahydro-1,3-dioxo-4-isoquinolinecarboxylic Acid Methyl Ester A mixture of (2-carboxyphenyl)propanedioic acid dimethyl ester (5.0 g, 19.84 mmol) and SOCl$_2$ (20 g) was refluxed for 1½ hours. The volatiles were removed in vacuo and the acid chloride was dissolved in THF (20 mL). In a second flask were placed 4-bromo-2-fluorobenzylamine (4.67 g, 22.91 mmol), triethylamine (15.96 mL, 114.55 mmol) and THF (150 mL). The contents of the first flask were added into the second flask and the mixture was stirred for 30 minutes. The formed suspension was poured into H$_2$O (1000 mL), stirred for 10 minutes and acidified with HCl (2N). The mixture was extracted with EtOAc and the organic layer was dried over MgSO$_4$. Evaporation gave a yellowish solid which was recrystallized from acetone/ether/hexane (at −20° C.) to yield a white solid (6.91 g, m.p. 149°-150° C.).

NMR (DMSO-d$_6$, 400 MHz): δ [3.67, 3.99 (s, 3H, —CO$_2$CH$_3$, tautomeric)], 5.06 (q, J=15.4 Hz), 5.29 (s, 2H, N—CH$_2$—, tautomeric], 5.03 (s, 1H, —CHCO$_2$CH$_3$, tautomeric), 7.07-8.44 (m, 7H, Ar—H̲, tautomeric).

IR (KBr, cm$^{-1}$): 1675 (s), 1610 (s), 1490 (s), 795 (m).

MS (m/e): 405 (M$^+$), 373 (M$^+$—MeOH).

Anal. Calcd.: C, 53.22; H, 3.23; N, 3.45. Found: C, 52.91; H, 3.20; N, 3.27.

The following compound was prepared in substantially the same manner as that of Example 1, step (d).

2-[(4-Bromo-2-fluorophenyl)methyl]-6-fluoro-1,2,3,4-tetrahydro-1,3-dioxo-4-isoquinolineacetic Acid Methyl Ester NMR (DMSO-d$_6$, 400 MHz): δ 3.98 (s, 3H, —CO$_2$CH$_3$), 5.27 (s, 2H, —NCH$_2$—), 7.08 (t, J=7.95 Hz, 1H, Ar—H̲), 7.2 (m, 1H, Ar—H̲), 7.34 (m, 2H, Ar—H̲, —OH), 7.54 (m, 1H, Ar—H̲), 8.1-8.26 (m, 2H, Ar—H̲).

IR (KBr, cm$^{-1}$): 1680 (s), 1660 (s), 1610 (s), 785 (m).

MS (m/e): 423 (M$^+$), 391 (M$^+$—CH$_3$OH).

Anal. Calcd.: C, 50.97; H, 2.85; N, 3.30. Found: C, 50.86; H, 2.86; N, 3.33.

M.P. 157°-158° C.

Step (e) Preparation of 1,2,3,4-Tetrahydro-4-(methoxycarbonyl)-2-methyl-1,3-dioxo-4-isoquinolineacetic Acid 1,1-Dimethylethyl Ester To a suspension of 1,2,3,4-tetrahydro-2-methyl-1,3-dioxo-4-isoquinolinecarboxylic acid methyl ester (5.5 g, 23.6 mmol), K$_2$CO$_3$ (3.91 g, 28.33 mmol) in DMF (100 mL) was added tert-butyl bromoacetate (4.57 mL, 28.33 mmol). After stirring at 70° C. for 1 hour, the mixture was poured into H$_2$O, extracted with EtOAc and dried over MgSO$_4$. The crude product was purified by flash chromatography (hexane/EtOAc, 3/1) to yield a white solid m.p. 89°-90° C. (7.3 g, 89.0%).

NMR (DMSO-d$_6$, 200 MHz): δ 1.01 (s, 9H, —CO$_2$-tert-butyl), 3.31 (s, 3H, NCH$_3$), 3.58 (m, 5H, —CO$_2$CH$_3$, —CH$_2$CO$_2$C(CH$_3$)$_3$), 7.61 (m, 2H), 7.74 (dt, J=7.6 Hz, 1.6 Hz, 1H, Ar—H̲), 8.18 (dd, J=8.4 Hz, 2.0 Hz, 1H, Ar—H̲).

IR (KBr, cm$^{-1}$): 3420 (m), 1750 (s), 1730 (s), 1670 (s), 1465 (m), 740 (m).

M/S (m/e): 347 (M$^+$).

Anal. Calcd.: C, 62.24; H, 6.09; N, 4.03. Found: C, 62.20; H, 6.08; N, 4.02.

The following compound was prepared in substantially the same manner as that of Example 1, Step (e).

2-[(4-Bromo-2-fluorophenyl)methyl]-1,2,3,4-tetrahydro-4-(methoxycarbonyl)-1,3-dioxo-4-isoquinolineacetic Acid 1,1-Dimethylethyl Ester NMR (DMSO-d$_6$, 400 MHz): δ 1.04 [s, 9H, —C(CH$_3$)$_3$], 3.53 (s, 3H, —CO$_2$CH$_3$), 3.60 [dd, J=17.7 Hz, 2H, —CH$_2$CO$_2$C(CH$_3$)$_3$], 5.14 (s, 2H, NCH$_2$—), 7.17 (t, J=8.25 Hz, 1H, Ar—H̲), 7.36 (dd, J=8.36 Hz, 1.75 Hz, 1H, Ar—H̲), 7.6 (m, 3H, Ar—H̲), 7.77 (dt, J=7.2 Hz, 1.27 Hz, 1H, Ar—H̲), 8.19 (dd, J=8.25 Hz, 1.54 Hz, 1H, Ar—H̲).

IR (CHCl$_3$, cm$^{-1}$): 1720 (s), 1675 (s), 1360 (s), 765 (m).

M/S (m/e): 520 (M+H)$^+$, 464 [M$^+$—C(CH$_3$)$_3$].

Step (f) Preparation of 1,2,3,4-Tetrahydro-4-(methoxycarbonyl)-2-methyl-1,3-dioxo-4-isoquinolineacetic Acid A mixture of 1,2,3,4-tetrahydro-4-(methoxycarbonyl)-2-methyl-1,3-dioxo-4-isoquinolineacetic acid 1,1-dimethylethyl ester (5.5 g, 15.85 mmol), CH$_2$Cl$_2$ (25 mL) and CF$_3$CO$_2$H (5 mL) was stirred at room temperature for 10 hours. The volatiles were removed in vacuo and the residue was recrystallized from ether/acetone/hexane (at −20° C.) to yield a white solid m.p. 188°-189° C. (4.35 g, 94.36%).

NMR (DMSO-d$_6$, 200 MHz): δ 3.28 (s, 3H, N—CH$_3$), 3.57 (s, 3H, —CO$_2$CH$_3$), 3.61 (s, 2H, —CH$_2$CO$_2$H), 7.54 (m, 2H, Ar—H̲), 7.75 (dt, J=8.2 Hz, 1.6 Hz, 1H, Ar—H̲), 8.18 (d, J=7.8 Hz, 1H, Ar—H̲), 12.3 (brs, 1H, —CO$_2$H).

IR (KBr, cm$^{-1}$): 3420 (m), 3500-2500 (brs), 1755 (s), 1730 (s), 1710 (s), 1660 (s), 1455 (m), 745 (m).

M/S (m/e): 291 (M+).

Anal. Calcd.: C, 57.73; H, 4.50; N, 4.81. Found: C, 57.55; H, 4.68; N, 4.75.

The following compounds were prepared in substantially the same manner as that of Example 1, Step (f).

2-[(4-Bromo-2-fluorophenyl)methyl]-1,2,3,4-tetrahydro-4-(methoxycarbonyl)-1,3-dioxo-4-isoquinolineacetic Acid NMR (DMSO-d$_6$, 400 MHz): δ 3.54 (s, 3H, —CO$_2$CH$_3$), 3.64 (q, J=17.67 Hz, 2H, —CH$_2$CO$_2$H), 5.12 (q, J=15.34 Hz, 2H, —NCH$_2$—), 7.14 (t, J=8.22 Hz, 1H, Ar—H), 7.3 (d, J=8.3 Hz, 1H, Ar—H), 7.5-7.6 (m, 3H, Ar—H), 7.76 (d, 7.4 Hz, 1H, Ar—H), 8.16 (d, J=7.8 Hz, 1H, Ar—H), 12.35 (s, 1H, —CO$_2$H).

IR (KBr, cm$^{-1}$): 3280 (m), 3500-2500 (br), 1750 (s), 1720 (s), 1675 (s), 1350 (s), 875 (m).

M/S (m/e): 463 (M+), 445 (M+—H, —OH).

Anal. Calcd. for C$_{20}$H$_{15}$BrFNO$_6$.0.2H$_2$O: C, 51.28; H, 3.30; N, 2.99. Found: C, 51.26; H, 3.48; N, 2.95.

M.P. 139°-140° C.

2-[(4-Bromo-2-fluorophenyl)methyl]-6-fluoro-1,2,3,4-tetrahydro-4-(methoxy-carbonyl)-1,3-dioxo-4-isoquinolineacetic Acid NMR (DMSO-d$_6$, 400 MHz): δ 3.56 (s, 3H, —CO$_2$CH$_3$), 3.6 (d, J=17.9 Hz, 1H, —CH$_2$CO$_2$H), 3.8 (d, J=17.9 Hz, 1H, —CH$_2$CO$_2$H), 5.1 (dd, J=15.5 Hz, 2H, —NCH$_2$—), 7.12 (t, J=8.23 Hz, 1H, Ar—H), 7.31 (dd, J=8.28 Hz, 1.68 Hz, 1H, Ar—H), 7.45 (dt, J=8.56 Hz, 2.5 Hz, 1H, Ar—H), 7.54 (dd, J=9.77 Hz, 1.89 Hz, 1H, Ar—H), 7.64 (dd, J=9.61 Hz, 2.46 Hz, 1H, Ar—H), 8.23 (dd, J=8.79 Hz, 5.81 Hz, 1H, Ar—H), 12.67 (br s, 1H, —CO$_2$H)

IR (KBr, cm$^{-1}$): 3400-2700 (br), 1745 (s), 1710 (s), 1670 (s), 770 (m).

M/S (m/e): 481 (M+), 405 (M$^{30}$ —CO$_2$—CH$_3$OH).

Anal. Calcd.: C,49.81; H, 2.93; N, 2.90. Found: C, 49.94; H, 3.03; N, 2.84.

M.P. 132°-133.5° C.

2-[(4-Bromo-2-fluorophenyl)methyl]-1,2,3,4-tetrahydro-4-(ethoxycarbonyl)-1,3-dioxo-4-isoquinolineacetic Acid NMR (DMSO-d$_6$, 400 MHz): δ 0.89 (t, J=7.04 Hz, 3H, —CO$_2$CH$_2$CH$_2$CH$_3$), 3.62 (dd, J=17.75 Hz, 1H, —CH$_2$CO$_2$H), 3.96 (dq, J=7.14 Hz, 2H, —CO$_2$CH$_2$CH$_3$, diastereomeric), 5.1 (dd, J=15.24 Hz, 2H, —NCH$_2$—), 7.17 (t, J=8.17 Hz, 1H, Ar—H), 7.3 (dd, J=8.26 Hz, 1.7 Hz, 1H, Ar—H), 7.54 (dd, J=9.83 Hz, 1.9 Hz, 1H, Ar—H), 7.57-7.62 (m, 2H, Ar—H), 7.76 (dt, J=7.57 Hz, 1.34 Hz, 1H, Ar—H), 8.16 (dd, J=7.82 Hz, 1.2 Hz, 1H, Ar—H), 12.64 (s, 1H, —CO$_2$H);

IR (KBr, cm$^{-1}$): 3450-2700 (br), 1750 (s), 1720 (s), 1680 (s), 750 (m).

M/S (m/e): 477 (M+).

Anal. Calcd.: C, 52.74; H, 3.58; N, 2.93. Found: C, 52.67; H, 3.74; N, 2.94.

Step(f) Preparation of 2[(3,4-Dichlorophenyl)methyl]-1,2,3,4-tetrahydro-1,3-dioxo-4-isoquinolineacetic Acid A mixture of 2-[(3,4-dichlorophenyl)methyl]-1,2,3,4-tetrahydro-1,3-dioxo-4-isoquinolineacetic acid, 1,1 dimethylethyl ester (2.0 g, 4.6 mmol), CH$_2$Cl$_2$ (80 mL) and CF$_3$CO$_2$H (6 mL) was stirred at room temperature for 2 hours. The volatiles were removed in vacuo, and the residue was purified by flash chromatography (acid washed silica gel, 5%, H$_3$PO$_4$/MeOH) to yield a white solid, m.p. 161°-163° C. (1.1 g, 63.2%).

NMR (DMSO-d$_6$, 400 MHz): δ 3.34 (m, 2H, CH$_2$CO$_2$H), 4.36 (t, J=3.6 Hz, 1H, —CHCH$_2$CO$_2$H), 5.07 (q, J=15.16 Hz, 2H, —NCH$_2$C$_6$H$_3$Cl$_2$), 7.3 (dd, J=8.3 Hz, 2.08 Hz, 1H, Ar—H), 7.44-7.6(m,4H, Ar—H), 7.7 (dt, J=7.7 Hz, 1.5 Hz, 1H, Ar—H), 8.07 (dd, 7.86 Hz, 1.3 Hz, 1H, Ar—H).

IR (KBr, cm$^{-1}$): 3440 (m), 3500-2500 (brm), 1710 (s), 1670 (s), 1335 (s), 965 (m), 765 (m).

M/S (m/e): 377 (M+), 218 (M+—CH$_2$C$_6$H$_3$Cl$_2$).

Anal. Calcd.: C, 57.16; H, 3.46; N, 3.70. Found: C, 56.91; H, 3.63; N, 3.65.

Step(g) Preparation of 2-[(4-Bromo-2-fluorophenyl)methyl]-1,2,3,4-tetrahydro-1,3-dioxo-4-isoquinolineacetic Acid To a solution of 2-[(4-bromo-2-fluorophenyl)methyl]-1,2,3,4-tetrahydro-4-(ethoxycarbonyl)-1,3-dioxo-4-isoquinolineacetic acid (2.2 g, 4.6 mmol) in THF (30 mL) and MeOH (30 mL) was added aqueous NaOH (2.5N, 15 mL). After stirring for 30 minutes, the mixture was poured into H$_2$O (1000 mL), acidified with HCl (2N) and extracted with EtOAc. The organic extracts were dried over MgSO$_4$. Evaporation and crystallization from ethyl ether/hexane gave a white solid (1.25 g).

NMR (DMSO-d$_6$, 400 MHz): δ 3.34 (d, 2H, —CH$_2$CO$_2$H), 4.36 (t, J=4.11 Hz, 1H, ArCHCH$_2$CO$_2$H), 5.05 (dd, J=15.5 Hz, 2H, —NCH$_2$—), 7.2 (t, J=8.13 Hz, 1H, Ar—H), 7.23 (dd, J=8.35 Hz, 1.76 Hz, 1H, Ar—H), 7.48 (t, J=7.57 Hz, 1H, Ar—H), 7.52 (dd, J=9.77 Hz, 1.78 Hz, 1H, Ar—H), 7.58 (d, J=7.83 Hz, 1H, Ar—H), 7.70 (dt, J=7.73 Hz, 1.2 Hz, 1H, Ar—H), 8.06 (dd, J=7.86 Hz, 1.02 Hz, 1H, Ar—H), 12.43 (s, 1H, —CO$_2$H).

IR (KBr, cm$^{-1}$): 3350-2200 (br), 1730 (s), 1710 (s), 1670 (s).

M/S (m/e): 405 (M+), 387 (M+—H$_2$O).

Anal. Calcd.: C, 53.22; H, 3.23; N, 3.45. Found: C, 52.88; H, 3.49; N, 3.57.

The following compound was prepared in substantially the same manner as that of Example 1, Step (g).

2-[(4-Bromo-2-fluorophenyl)methyl]-6-fluoro-1,2,3,4-tetrahydro-1,3-dioxo-4-isoquinolineacetic Acid NMR (DMSO-d$_6$, 400 MHz): δ 3.43 (m, 2H, —CH$_2$CO$_2$H), 4.37 (t, J=4.09 Hz, 1H, ArCHCH$_2$), 5.03 (dd, J=15.4 Hz, 1H, —NCH$_2$), 7.15 (t, J=8.21 Hz, 1H, Ar—H), 7.23 (dd, J=8.35 Hz, 1.81 Hz, 1H, Ar—H), 7.31 (dt, J=8.48 Hz, 2.14 Hz, 1H, Ar—H), 7.51-7.56 (m, 2H, Ar—H), 8.12 (dd, J=8.77 Hz, 5.94 Hz, 1H, Ar—H), 12.46 (s, 1H, —CO$_2$H).

IR (KBr, cm$^{-1}$): 3400-2400 (br), 1725 (s), 1710 (s), 1670 (s).

M/S (m/e): 423 (M+), 405 (M+—H$_2$O).

Anal. Calcd.: C, 50.97; H, 2.85; N, 3.30. Found: C, 50.75; H, 2.64; N, 3.18.

Step (h) Preparation of 4-(2-Amino-2-oxoethyl)-2-[(4-Bromo-2-fluorophenyl)methyl]-1,2,3,4-tetrahydro-1,3-dioxo-4-isoquinolinecarboxylic Acid Methyl Ester A mixture of 2-[(4-bromo-2-fluorophenyl)methyl]-1,2,3,4-tetrahydro-4-(methoxycarbonyl)-1,3-dioxo-4-isoquinolineacetic acid (4.0 g, 8.62 mmol) and SOCl$_2$ (20 g), was refluxed for 1 hour. The volatiles were removed in vacuo and the acid chloride was dissolved in THF (20 mL). In a second flask was placed a freshly prepared saturated NH$_3$/THF solution (100 mL) and the contents of the first flask were added slowly. After the addition, the mixture was stirred for 10 minutes, poured into H$_2$O (500 mL), acidified with HCl (2N) and extracted with EtOAc. The organic extracts were dried over MgSO$_4$, and evaporated to give an off-white solid. The crude product was recrystallized from ether/hexane (at −20° C.) to yield a white solid (3.55 g, m.p. 180°–181° C.).

NMR (DMSO-d$_6$, 400 MHz): δ 3.53 (s, 3H, —CO$_2$CH$_3$), 3.55 (dd, J=16.6 Hz, 2H, —CH$_2$CONH$_2$), 5.12 (dd, J=15.5 Hz, 2H, —NCH$_2$—), 6.88 (s, 1H, —CONH—), 7.23 (t, J=8.25 Hz, 1H, Ar—H), 7.3 (dd, J=8.36 Hz, 1.8 Hz, 1H, Ar—H), 7.45 (d, J=7.9 Hz, 1H, Ar—H), 7.5–7.58 (m, 3H, Ar—H, —CONH), 7.75 (dt, J=7.63 Hz, 1.4 Hz, 1H, Ar—H), 8.13 (dd, J=7.8 Hz, 1.17 Hz, 1H, Ar—H).

IR (KBr, cm$^{-1}$): 3440 (s), 1730 (s), 1715 (s), 745 (m).

MS (m/e): 463 (M+H)$^+$.

Anal. Calcd.: C, 51.85; H, 3.48; N, 6.05. Found: C, 51.73; H, 3.30; N, 5.94.

The following compound was prepared in substantially the same manner as that of Example 1, Step h).

4-(2-Amino-2-oxoethyl)-2-[(4-bromo-2-fluorophenyl)-methyl]-6-fluoro-1,2,3,4-tetrahydro-1,3-dioxo-4-isoquinolinecarboxylic Acid Methyl Ester NMR (DMSO-d$_6$, 400 MHz): δ 3.49 (d, J=16.65 Hz, 1H, —CH$_2$CONH$_2$), 3.56 (s, 3H, —CO$_2$CH$_3$), 3.59 (d, J=16.65 Hz, 1H, —CH$_2$CONH$_2$), 5.08 (dd, J=15.48 Hz, 2H, —NCH$_2$—), 6.94 (s, 1H, —CONH$_2$), 7.21 (t, J=8.22 Hz, 1H, Ar—H), 7.30 (dd, J=8.27 Hz, 1.64 Hz, 1H, Ar—H), 7.38–7.46 (m, 2H, Ar—H), 7.51 (s, 1H, —CONH$_2$), 7.54 (dd, J=9.81 Hz, 1.83 Hz, 1H, Ar—H), 8.20 (dd, J=8.74 Hz, 5.84 Hz, 1H, Ar—H).

IR (KBr, cm$^{-1}$): 3440 (s), 3350 (s), 1740 (s), 1710 (s), 1670 (s), 1660 (s), 765 (m).

MS (m/e): 480 (M+), 463 (M+—NH$_3$).

Anal. Calcd.: C, 49.91; H, 3.14; N, 5.82. Found: C, 49.56; H, 3.09; N, 5.73.

M.P. 203°–204.5° C.

Step (i) Preparation of 4-(2-Amino-2-oxoethyl)-1,2,3,4-tetrahydro-2-methyl-1,3-dioxo-4-isoquinolinecarboxylic Acid Methyl Ester To a solution of 1,2,3,4-tetrahydro-4-(methoxycarbonyl)-2-methyl-1,3-dioxo-4-isoquinolineacetic acid (3.2 g, 10.98 mmol) in DMF (50 mL) were added 1-(3-dimethylaminopropyl)-3-ethylcarbodiimide hydrochloride (2.74 g, 14.29 mmol), 1-hydroxybenzotriazole hydrate (2.22 g, 16.5 mmol), and the mixture was stirred for 2 hours. A freshly prepared tetrahydrofuran ammonium solution was added dropwise with continuous monitoring of the reaction by thin layer chromatography (TLC). Upon completion of the reaction, the mixture was poured into H$_2$O, acidified with HCl (2N), extracted with EtOAc, and dried over MgSO$_4$. The crude product was purified by flash chromatography (hexane/EtOAc 1/1) to yield a white solid, m.p. 230°–231° C. (2.6 g, 81.76%).

NMR (DMSO-d$_6$, 200 MHz): δ 3.27 (s, 3H, —NCH$_3$), 3.49 (s, 2H, —CH$_2$CO$_2$H), 3.56 (s, 3H, —CO$_2$CH$_3$), 6.78 (s, 1H, —CONH$_2$), 7.4–7.6 (m, 3H, Ar—H, —CONH$_2$), 7.69 (dt, J=7.6 Hz, 2 Hz, 1H, Ar—H), 8.16 (d, J=8.2 Hz, 1H, Ar—H).

IR (KBr, cm$^{-1}$): 3420 (m), 3320 (cm), 1760 (s), 1660 (s), 1420 (m), 755 (m).

M/S (m/e): 290 (M+).

Anal. Calcd.: C, 57.93; H, 4.86; N, 9.65. Found: C, 57.73; H, 4.95; N, 9.56.

The following compounds were obtained in substantially the same manner as that of Example 1, Step (e).

4-(2-Amino-2-oxoethyl)-6-chloro-1,2,3,4-tetrahydro-2-methyl-1,3-dioxo-4-isoquinolinecarboxylic Acid Methyl Ester NMR (DMSO-d$_6$, 200 MHz): δ 3.26 (s, 3H, —NCH$_3$), 3.51 (q, J=17.5 Hz, 2H, —CH$_2$CONH$_2$), 3.59 (s, 3H, —CO$_2$CH$_3$), 6.85 (s, 1H, —CONH$_2$), 7.5 (s, 1H, —CONH$_2$), 7.53 (d, J=2.0 Hz, 1H, Ar—H), 7.62 (dd, J=8.6 Hz, 2.0 Hz, 1H, Ar—H), 8.16 (d, J=8.0 Hz, 1H, Ar—H).

IR (KBr, cm$^{-1}$): 3420 (s), 1760 (s), 1710 (m), 1660 (s), 1235 (m), 770 (m).

M/S (m/e): 324 (M+).

Anal. Calcd.: C, 51.78; H, 4.03; N, 8.63. Found: C, 51.67; H, 3.95; N, 8.42.

M.P. 221°–222° C.

4-(2-Amino-2-oxoethyl)-7-chloro-1,2,3,4-tetrahydro-2-methyl-1,3-dioxo-4-isoquinolinecarboxylic Acid Methyl Ester NMR (DMSO-d$_6$, 400 MHz): δ 3.27 (s, 3H, —NCH$_3$), 3.48 (s, 2H, —CH$_2$CONH$_2$), 3.58 (s, 3H, —CO$_2$CH$_3$), 6.85 (s, 1H, —CONH$_2$), 7.45 (d, J=8.6 Hz, 1H, Ar—H), 7.49 (s, 1H, —CONH$_2$), 7.80 (dd, J=8.2 Hz, 2.2 Hz, 1H, Ar—H), 8.08 (d, J=2.2 Hz, 1H, Ar—H).

IR (KBr, cm$^{-1}$): 3420 (s), 1760 (s), 1715 (m), 1665 (s), 1440 (m), 770 (m).

M/S (m/e): 324 (M+).

Anal. Calcd.: C, 51.78; H, 4.03; N, 8.63. Found: C, 51.82; H, 3.98; N, 8.54.

M.P. 215°–216° C.

Step (j); Preparation of [[2-[(4-Bromo-2-fluorophenyl)methyl]-6-fluoro-1,2,3,4-tetrahydro-1,3-dioxo-4-isoquinolinyl]acetyl]carbamic Acid Methyl Ester To a solution of 4-(2-amino-2-oxoethyl)-2-[(4-bromo-2-fluorophenyl)-methyl]-6-fluoro-1,2,3,4-tetrahydro-1,3-dioxo-4-isoquinolinecarboxylic acid methyl ester (4.5 g, 9.63 mmol) in EtOH (50 mL) was added K$_2$CO$_3$ (6.65 g, 48.19 mmol) and the mixture was stirred at room temperature for 1 hour. The yellow suspension was poured into H$_2$O (1000 mL), acidified with HCl (2N) and extracted with EtOAc. The organic extracts were dried over MgSO$_4$. Evaporation and purification by flash chromatography (hexane/EtOAc 3/1) yielded a white solid (2.2 g, m.p. 162°–163° C.).

NMR (DMSO-d$_6$, 400 MHz): δ 3.62 (m, 5H, —CO$_2$CH$_3$, —CH$_2$CONHCO$_2$CH$_3$), 4.43 (t, J=4.1 Hz, 1H, Ar—CHCH$_2$CO—), 5.03 (s, 2H, —NCH$_2$—), 7.15 (t, J=8.27, 1H, Ar—H), 7.25 (dd, J=8.4 Hz, 1.75 Hz, 1H, Ar—H), 7.31 (dt, J=8.5 Hz, 2.3 Hz, 1H, Ar—H), 7.44 (dd, J=8.5 Hz, 2.3 Hz, 1H, Ar—H), 7.52 (dd, J=9.81 Hz, 1.83 Hz, 1H, Ar—H), 8.13 (dd, J=8.73 Hz, 6.0 Hz, 1H, Ar—H), 10.72 (s, 1H, —CONHCO$_2$CH$_3$).

IR (KBr, cm$^{-1}$): 3410 (s), 1760 (s), 1720 (s), 1680 (s).

M/S (m/e): 481 (M+H)$^+$.

Anal. Calcd.: C, 49.91; H, 3.14; N, 5.82. Found: C, 49.81; H, 3.01; N, 5.54.

The following compound was prepared in substantially the same manner as that of Example 1, Step (j).

[(7-Chloro-1,2,3,4-tetrahydro-2-methyl-1,3-dioxo-4-isoquinolinyl)acetyl]-carbamic Acid Methyl Ester NMR (DMSO-d$_6$, 400 MHz): δ [3.2 (s), 3H, N—CH$_3$, tautomeric], 3.6 (m, 5H, —CO$_2$CH$_3$, —CH$_2$CO—), [4.29 (t), J=4.2 Hz, 6.75 (s), 1H, ArCHCH$_2$—, —OH, tautomeric], 7.5–8.0 (m, 3H, Ar-H, tautomeric), [10.63 (s), 10.69 (s), 1H, —CONHCO$_2$Me, tautomeric].

IR (KBr, cm⁻¹): 3360 (s), 1755 (s), 1740 (s), 1710 (s), 1670 (s).

M/S (m/e): 324 (M+), 249 (M+—NH₂CO₂CH₃).

Anal. Calcd.: C, 51.78; H, 4.03; N, 8.63. Found: C, 51.08; H, 3.81; N, 8.41.

M.P. 173°-174° C.

Step (k) Preparation of [(1,2,3,4-Tetrahydro-2-methyl-1,3-dioxo-4-isoquinolinyl)acetyl]carbamic Acid Methyl Ester To a solution of 4-(2-amino-2-oxoethyl)-1,2,3,4-tetrahydro-2-methyl-1,3-dioxo-4-isoquinolinecarboxylic acid methyl ester (2.0 g, 6.89 mmol) in DMF (20 mL) was added NaH (80% dispersion in oil, 206.9 mg, 6.89 mmol) portionwise over a 10 minute period.

After stirring for 30 minutes, the mixture was poured into H₂O, acidified with HCl (2N), extracted with EtOAc, and dried over MgSO₄. The crude product was purified by flash chromatography, on acid washed silica gel (5% H₃PO₄/MeOH) to yield a white solid, m.p. 169°-170° C. (1.2 g, 64.5%).

NMR (DMSO-d₆, 400 MHz): δ 3.20 (s, 3H, —NCH₃), 3.55 (m, 2H, —CH₂CONHCO₂Me), 3.61 (s, 3H, —NH-CO₂Me), 4.29 (t, J=4.13 Hz, 1H, —CH(CH₂CONH-CO₂Me)CO—), 7.46 (m, 2H, Ar—H), 7.64 (t, J=7.7 Hz, 1H, Ar—H), 8.07 (d, J=7.8 Hz, 1H, Ar—H), 10.67 (s, 1H, —CONHCO₂Me).

IR (KBr, cm⁻¹): 1780 (s), 1715 (s), 1650 (s), 1510 (s), 750 (m).

M/S (m/e): 290 (M+), 216 (M+—NHCO₂Me), 188 (M+—NHCO₂Me, —CO).

Anal. Calcd.: C, 57.93; H, 4.86; N, 9.65. Found: C, 57.83; H, 4.98; N, 9.52.

The following compounds were prepared in substantially the same manner as that of Example 1, Step k).

[(6-Chloro-1,2,3,4-tetrahydro-2-methyl-1,3-dioxo-4-isoquinolinyl)acetyl]-carbamic Acid Ethyl Ester NMR (400 MHz, DMSO-d₆): δ 1.18 (t, J=7.16 Hz, 3H, —CO₂CH₂CH₃, 3.19 (s, 3H, —NCH₃), 3.6 (dd, J=18.4 Hz, 4.1 Hz, 2H, —CH₂CONHCO₂CH₃), 4.09 (q, J=7.06 Hz, 2H, —CO₂CH₂CH₃), 4.29 (t, J=4.14 Hz, 1H, —CHCH₂CO—), 7.5 (dd, J=8.4 Hz, 1.70 Hz, 1H, Ar—H), 7.62 (d, J=0.92 Hz, 1H, Ar—H), 8.06 (d, J=8.4 Hz, 1H, Ar—H), 10.6 (s, 1H, —CONH CO₂CH₂CH₃).

IR (cm⁻¹): 3240(s), 1765(s), 1715(s), 1695(s), 1665(s), 1490(s), 780(s).

M/S (m/e): 339(M+H)+.

Anal. Calcd.: C, 53.34; H 4.18; N 8.29, Found: C, 52.98; H 4.52; N 8.19,

M.P. 152°-153° C.

[(6-Chloro-1,2,3,4-tetrahydro-2-methyl-1,3-dioxo-4-isoquinolinyl)acetyl]carbamic Acid Methyl Ester NMR (DMSO-d₆, 400 MHz): δ 3.2 (s, 3H, —NCH₃), 3.6 (m, 5H, —CO₂CH₃, —CH₂CO₂H), 4.29 (t, J=4.15 Hz, 1H, ArCHCH₂CO₂H), 7.5 (dd, J=8.45 Hz, 0.9 Hz, 1H, Ar—H), 7.62 (d, J=0.9 Hz, 1H, Ar—H), 8.04 (d, J=8.46 Hz, 1H, Ar—H), 10.68 (s, 1H, —CONH CO₂CH₃), IR (KBr, cm⁻¹): 3350 (s), 1745 (s), 1710 (s), 1660 (s), M/S (m/e): 324 (M+), 249 (M+—NHCO₂Me), 221 (M+—CONHCO₂Me), Anal. Calcd.: C, 51.78; H, 4.03; N, 8.63, Found: C, 51.76; H, 4.03; N, 8.49,

M.P. 184°-186° C.

We claim:

1. The compounds of formula (I)

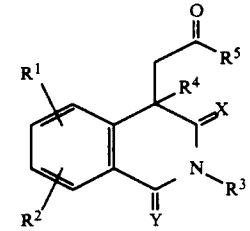

wherein R¹ and R² are independently hydrogen, alkyl consisting of 1 to 6 carbon atoms, halogen, lower alkoxy consisting of 1 to 6 carbon atoms, trifluoromethyl, lower alkylthio wherein lower alkyl consists of 1 to 6 carbon atoms, dialkylamino wherein alkyl consists of 1 to 6 carbon atoms, nitro, aryl or aryl(lower alkyl) oxy wherein aryl consists of 6 to 10 carbon atoms and lower alkyl consists of 1 to 6 carbon atoms; R³ is lower alkyl consisting of 1 to 6 carbon atoms, halogen substituted aryl (lower alkyl) wherein aryl consists of 6 to 10 carbon atoms and lower alkyl consists of 1 to 6 carbon atoms, acyl or heterocyclic (lower alkyl) of structural formula

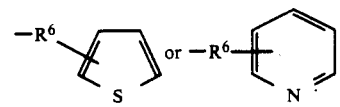

wherein R⁶ is lower alkylene consisting of 1 to 3 carbon atoms; R⁴ is hydrogen; R⁵ is amino, hydroxy, lower alkyl carbamates wherein lower alkyl consists of 1 to 6 carbon atoms, aryl carbamates wherein aryl consists of 6 to 10 carbon atoms, and aryl(lower alkyl) carbamates wherein lower alkyl consists of 1 to 6 carbon atoms; X and Y are oxygen or sulfur, or the pharmaceutically acceptable salts thereof with the proviso that when R⁵ is hydroxy R¹ and R² are not both hydrogen and R³ is not lower alkyl consisting of 1 to 6 carbon atoms.

2. The compounds having the structural formula (III)

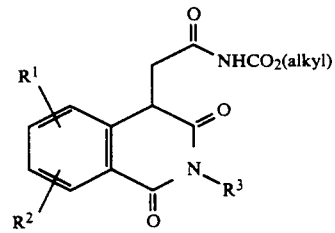

wherein R¹ and R² are independently hydrogen or halogen; R³ is lower alkyl consisting of 1 to 6 carbon atoms, or halogen substituted aryl (lower alkyl) wherein aryl consists of 6 to 10 carbon atoms and lower alkyl consists of 1 to 6 carbon atoms or the pharmaceutically acceptable salts thereof.

3. The compounds having the structural formula (IV)

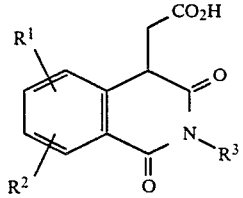

wherein $R^1$ and $R^2$ are halogen; $R^3$ is halogen substituted aryl (lower alkyl) wherein aryl consists of 6 to 10 carbon atoms and lower alkyl consists of 1 to 6 carbon atoms or the pharmaceutically acceptable salts thereof.

4. The compound [(6-chloro-1,2,3,4-tetrahydro-2-methyl-1,3-dioxo-4-isoquinolinyl)acetyl]carbamic acid ethyl ester, or the pharmaceutically acceptable salts thereof.

5. The compound [(1,2,3,4-tetrahydro-2-methyl-1,3-dioxo-4-isoquinolinyl)acetyl]carbamic acid methyl ester, or the pharmaceutically acceptable salts thereof.

6. The compound [(6-chloro-1,2,3,4-tetrahydro-2-methyl-1,3-dioxo-4-isoquinolinyl)acetyl]carbamic acid methyl ester, or the pharmaceutically acceptable salts thereof.

7. The compound [(7-chloro-1,2,3,4-tetrahydro-2-methyl-1,3-dioxo-4-isoquinolinyl)acetyl]carbamic acid methyl ester, or the pharmaceutically acceptable salts thereof.

8. The compound [[2-[(4-bromo-2-fluorophenyl)methyl]-6-fluoro-1,2,3,4-tetrahydro-1,3-dioxo-4-isoquinolinyl]acetyl]carbamic acid methyl ester, or the pharmaceutically acceptable salts thereof.

9. The compound 2-[(4-bromo-2-fluorophenyl)methyl]-6-fluoro-1,2,3,4-tetrahydro-1,3-dioxo-4-isoquinolineacetic acid, or the pharmaceutically acceptable salts thereof.

10. A pharmaceutical composition for the treatment of neuropathy, nephropathy, retinopathy, or cataracts in a diabetic mammal, which comprises an effective amount of a compound of formula (I)

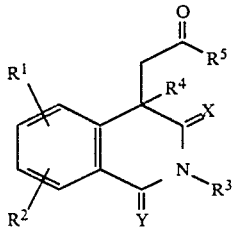

wherein $R^1$ and $R^2$ are independently hydrogen, alkyl consisting of 1 to 6 carbon atoms, halogen, lower alkoxy consisting of 1 to 6 carbon atoms, trifluoromethyl, lower alkylthio wherein lower alkyl consists of 1 to 6 carbon atoms, dialkylamino wherein alkyl consists of 1 to 6 carbon atoms, nitro, aryl or aryl(lower alkyl) oxy wherein aryl consists of 6 to 10 carbon atoms and lower alkyl consists of 1 to 6 carbon atoms; $R^3$ is lower alkyl consisting of 1 to 6 carbon atoms, aryl, aryl(lower alkyl) or halogen substituted aryl(lower alkyl) wherein aryl consists of 6 to 10 carbon atoms and lower alkyl consists of 1 to 6 carbon atoms, acyl or heterocyclic (lower alkyl) of structural formula

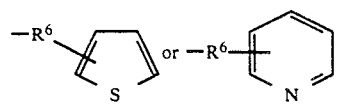

wherein $R^6$ is lower alkylene consisting of 1 to 3 carbon atoms; $R^4$ is hydrogen, lower alkyl consisting of 1 to 6 carbon atoms, carboalkoxy wherein alkoxy consists of 1 to 3 carbon atoms; $R^5$ is amino, hydroxy, alkoxy consisting of 1 to 6 carbon atoms, lower alkyl carbamates wherein lower alkyl consists of 1 to 6 carbon atoms, aryl carbamates wherein aryl consists of 6 to 10 carbon atoms, and aryl(lower alkyl) carbamates wherein lower alkyl consists of 1 to 6 carbon atoms; X and Y are oxygen or sulfur, or the pharmaceutically acceptable salts thereof.

11. A method of treatment of neuropathy, nephropathy, retinopathy, or cataracts in a diabetic mammal, which comprises administering to said mammal an effective amount of a compound of formula (I)

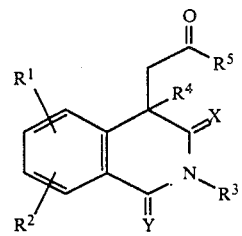

wherein $R^1$ and $R^2$ are independently hydrogen, alkyl consisting of 1 to 6 carbon atoms, halogen, lower alkoxy consisting of 1 to 6 carbon atoms, trifluoromethyl, lower alkylthio wherein lower alkyl consists of 1 to 6 carbon atoms, dialkylamino wherein alkyl consists of 1 to 6 carbon atoms, nitro, aryl or aryl(lower alkyl) oxy wherein aryl consists of 6 to 10 carbon atoms and lower alkyl consists of 1 to 6 carbon atoms; $R^3$ is lower alkyl consisting of 1 to 6 carbon atoms, aryl, aryl(lower alkyl) or halogen substituted aryl(lower alkyl) wherein aryl consists of 6 to 10 carbon atoms and lower alkyl consists of 1 to 6 carbon atoms, acyl or heterocyclic (lower alkyl) of structural formula

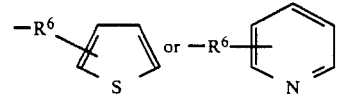

wherein $R^6$ is lower alkylene consisting of 1 to 3 carbon atoms; $R^4$ is hydrogen, lower alkyl consisting of 1 to 6 carbon atoms, carboalkoxy wherein alkoxy consists of 1 to 3 carbon atoms; $R^5$ is amino, hydroxy, alkoxy consisting of 1 to 6 carbon atoms, lower alkyl carbamates wherein lower alkyl consists of 1 to 6 carbon atoms, aryl carbamates wherein aryl consists of 6 to 10 carbon atoms, and aryl(lower alkyl) carbamates wherein lower alkyl consists of 1 to 6 carbon atoms; X and Y are oxygen or sulfur, or the pharmaceutically acceptable salts thereof.

* * * * *